(12) United States Patent
Yang et al.

(10) Patent No.: US 11,142,530 B2
(45) Date of Patent: Oct. 12, 2021

(54) DEEP-SEA FUNGUS-DERIVED ANTHRAQUINONE COMPOUND AND USE THEREOF IN PREPARING ANTI-ALLERGIC DRUGS

(71) Applicants: Third Institute of Oceanography, Ministry of Natural Resources, Xiamen (CN); China Ocean Mineral Resources R&D Association, Beijing (CN)

(72) Inventors: Xianwen Yang, Xiamen (CN); Cuiping Xing, Xiamen (CN); Jinmei Xia, Xiamen (CN)

(73) Assignees: Third Institute of Oceanography, Ministry of Natural Resources, Xiamen (CN); China Ocean Mineral Resources R&D Association, Beijing (CN)

( * ) Notice: Subject to any disclaimer, the term of this patent is extended or adjusted under 35 U.S.C. 154(b) by 1 day.

(21) Appl. No.: 16/726,835

(22) Filed: Dec. 25, 2019

(65) Prior Publication Data

US 2021/0198272 A1 Jul. 1, 2021

(51) Int. Cl.
*C07D 493/04* (2006.01)
*A61P 37/08* (2006.01)

(52) U.S. Cl.
CPC ............ *C07D 493/04* (2013.01); *A61P 37/08* (2018.01)

(58) Field of Classification Search
CPC ............................... C07D 493/04; A61P 37/08
See application file for complete search history.

(56) References Cited

PUBLICATIONS

Yanli Dou, et al., Metabolites from Aspergillus versicolor, an endolichenic fungus from the lichen Lobaria retigera, Drug Discoveries & Therapeutics, 2014, p. 84 88, vol. 8—No. 2.

*Primary Examiner* — Anna Pagonakis
(74) *Attorney, Agent, or Firm* — Bayramoglu Law Offices LLC

(57) ABSTRACT

An anthraquinone compound and the use thereof in preparing anti-allergic drugs. The anthraquinone compound has a structure according to formula (I) and can be used to prepare anti-allergic drugs.

Formula (I)

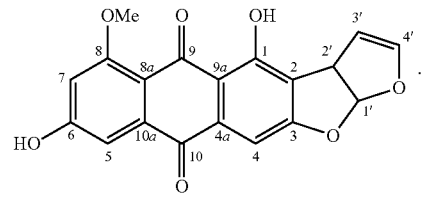

1 Claim, No Drawings

DEEP-SEA FUNGUS-DERIVED ANTHRAQUINONE COMPOUND AND USE THEREOF IN PREPARING ANTI-ALLERGIC DRUGS

TECHNICAL FIELD

The present invention relates to the field of marine microbial drug application, and particularly relates to an anthraquinone compound and the use thereof in preparing anti-allergic drugs.

BACKGROUND

Allergies are reproducible adverse reactions that are caused by the specific immune response of the immune system to allergens after a certain substance (such as food, drugs, etc.) enters the human body and affect different organs of the entire body, may cause multiple systemic reactions such as urticaria, nasal congestion and itching, wheezing, nausea and vomiting, and tachycardia. These reactions may be mild localized reactions or severe life-threatening reactions.

Allergy is a global health problem involving millions of patients. The results of epidemiological studies show that the prevalence of allergies has been increasing in the past 20 years, and currently recommended methods for treating allergies are still strictly preventing exposure to allergens. However, at present, allergens that have been medically identified are limited, and it is still impossible to effectively prevent allergic reactions caused by unknown allergens. Thus, people have an increasing urgency to find a therapy or even a radical treatment.

SUMMARY

One object of the present invention is, in view of the above-mentioned prior art issues, to provide the use of an anthraquinone compound in preparing anti-allergic drugs.

In order to realize the above object, the present invention provides the use of an anthraquinone compound and a salt thereof in preparing anti-allergic drugs, wherein the anthraquinone compound has a structure according to formula (I):

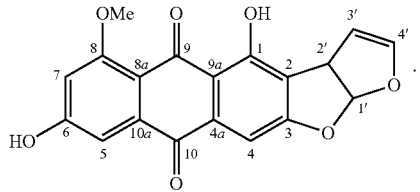

formula (I)

Specifically, the above-mentioned anthraquinone compound and the salt thereof can be used in preparing anti-allergic drugs.

The present invention also provides an anti-allergic drug or a drug for inhibiting mast cell degranulation, which comprises an effective dose of one or more of an anthraquinone compound and salts thereof as an active ingredient, and a pharmaceutically acceptable carrier.

The "salts" mentioned in the present invention include "pharmaceutically acceptable salts".

In the present invention, the "pharmaceutically acceptable carrier" should be understood as the excipients used in the pharmaceutical composition to provide the proper delivery of the active ingredient(s) to the subject.

The anthraquinone compound of the present invention is isolated from the fermentation product of a deep-sea fungus *Aspergillus nidulans*, and is determined by detailed structure analysis to have a structure according to formula (I), with a chemical formula as $C_9H_{12}O_7$.

It has been found through research that the anthraquinone compound has a strong inhibitory effect on mast cell degranulation, and thus can be used for preparing drugs for inhibiting mast cell degranulation. Mast cell is the major effector cell in allergic reactions and contains numerous basophilic granules in the cytoplasm. Immune-mediated or pharmacological-mediated stimulation will trigger degranulation and release of various active substances, such as histamines, leukotriene, platelet activating factor, and bradykinin, resulting in various allergic symptoms over the body. It is confirmed by further analysis that the compound exhibits a strong anti-allergic activity and can be used to prepare and develop anti-allergic drugs to treat allergic diseases.

The present invention also provides a method for preparing the above-mentioned anthraquinone compound, which comprises the following steps:

S1: fermenting *Aspergillus nidulans* to obtain a fermentation product; the *Aspergillus nidulans* is deposited with the Marine Culture Collection of China, with an accession number as MCCC 3A00050;

S2: subjecting the fermentation product to extraction, and subjecting an obtained extract to separation and purification to obtain the anthraquinone compound.

Specifically, the above method can be conducted with the following steps:

(1) culturing the *Aspergillus nidulans* in oats, subjecting to extraction with ethyl acetate, followed by addition of petroleum ether and dichloromethane to remove lipids, and concentrating to obtain a crude extract;

(2) subjecting the crude extract of step (1) to separation over a silica gel column by gradient elution with dichloromethane-methane;

(3) collecting a fraction where a volume ratio of dichloromethane-methane is 20:80 in step (2), and subjecting the fraction to separation over an ODS column by gradient elution with methane-water;

(4) collecting a fraction where a volume ratio of methane-water is ranging from 50:50 to 70:30 in step (3), and subjecting the fraction to separation over a dextran gel column by eluting with methane;

(5) collecting an eluate of step (4), drying by vacuum concentration to obtain the anthraquinone compound.

The present invention provide a novel compound for developing anti-allergic drugs, has great significance for the development of marine drugs, can promote the effective application of deep-sea biological resources, and has good application prospects.

DETAILED DESCRIPTION OF THE EMBODIMENTS

The present invention is further described below in combination with specific embodiments. It should be understood that the embodiments are not intended to limit the patent scope of the present invention. The parameters and proportions may be modified according to actual conditions.

Embodiment 1: Preparation of the Anthraquinone Compound (1) *Aspergillus nidulans* (purchased from the Marine Culture Collection of China, with an accession number as MCCC 3A00050) was added into forty 1L Erlenmeyer flasks containing 80 g of oats, cultured under static conditions at 25° C. for 40 days, and then the resultant was added with ethyl acetate for extraction, followed by addition of petroleum ether and dichloromethane to remove lipids, and concentrated under a low pressure to obtain a crude extract (100 g).

(2) The crude extract of step (1) was subjected to separation over a silica gel column (49×460 mm) by gradient elution with dichloromethane-methane ($CH_2Cl_2$-MeOH, from 100:0 to 0:100), so as to give seven fractions (Fr.1-Fr.7).

(3) The fifth fraction Fr.5 (where a volume ratio of dichloromethane-methane is 20:80) in step (2), was subjected to separation over an ODS column (26×310 mm) by gradient elution with methane-water (MeOH—$H_2O$, from 5:95 to 100:0), so as to give six sub-fractions (Fr.5.1-Fr.5.6).

(4) The six sub-fraction Fr.5.6 (where a volume ratio of methane-water is ranging from 50:50 to 70:30) in step (3), was subjected to separation over a Sephadex LH-20 dextran gel column (2×100 cm) by eluting with methane.

(5) Based on a TLC test result, an eluate of step (4) was collected and dried by vacuum concentration to obtain a product (4.2 mg).

The product in step (5) was subjected to structural identification.

The product is in the form of light yellow powders.

$^1$H-NMR (DMSO-$d_6$, 400 MHz): $\delta_H$ 13.64 (1H, s, 1-OH), 7.09 (1H, s, H-4), 7.20 (1H, d, J=2.2 Hz, H-5), 11.23 (1H, s, 6-OH), 6.84 (1H, d, J=2.2 Hz, H-7), 6.90 (1H, d, J=7.2 Hz, H-1'), 4.76 (1H, dt, J=7.2, 2.1 Hz, H-2'), 5.42 (1H, t, J=2.6 Hz, H-3'), 6.75 (1H, t, J=2.5 Hz, H-4'), 3.90 (3H, s, 8-OMe); $^{13}$C NMR (DMSO-$d_6$, 100 MHz): $\delta_C$ 158.8 (s, C-1), 120.7 (s, C-2), 163.4 (s, C-3), 100.1 (d, C-4), 107.1 (d, C-5), 164.3 (s, C-6), 105.5 (d, C-7), 162.5 (s, C-8), 186.0 (s, C-9), 181.8 (s, C-10), 112.9 (d, C-1'), 47.5 (d, C-2'), 101.6 (d, C-3'), 145.8 (d, C-4'), 134.2 (s, C-4a), 112.6 (s, C-8a), 112.3 (s, C-9a), 136.6 (s, C-10a), 56.3 (q, 8-OMe); ESIMS m/z 353 [M+H]+.

Based on the above data in combination with detailed 2D NMR, HRESIMS and OR analyses, the product is determined to be an anthraquinone compound with a chemical formula as $C_{19}H_{12}O_7$ and a structure according to formula (I):

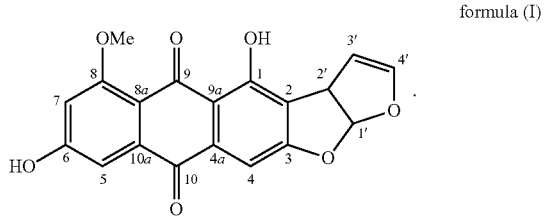 [SMILES: COc1cc(O)cc2c1C(=O)c1c(cc3c(c1O)C1C=COC1O3)C2=O]

formula (I)

Embodiment 2: In Vitro Anti-Allergic Activity Test of the Compound Prepared in Embodiment Currently available mast cell lines are not suitable for in vitro subculturing, and thus it is difficult to obtain a large number of homogeneous cells for experimental research. The RBL-2H3 cell line is similar to mast cells in cell structure and degranulation mechanism, and more importantly, it is possible to realize a stable subculturing of the line. Thus, the RBL-2H3 cell line is usually used as an alternative model of mast cells in the studies on mast cell functions and further researches of allergic diseases.

In the present embodiment, an IgE-mediated RBL-2H3 cell model was employed to measure the degranulation efficiency of sensitized cells, followed by a calculation to obtain the inhibitory of the compound against the cell degranulation and to further obtain the anti-allergic activity of the compound.

This embodiment was conducted with the following four groups:
(1) negative control group (non-activated group);
(2) blank control group (DNP-BSA-activated group);
(3) positive control group (loratadine group); and
(4) compound group (the compound obtained in step (5) in Embodiment 1).

This embodiment was conducted as follows:
(1) Sensitizing the cells: The RBL-2H3 cells were collected with trypsinization, and added into 96-well plates, 100 μL in each well, followed by the addition of anti-DNP-IgE to a final concentration of 1 μg/mL to sensitize the cells, and incubated in an incubator overnight (37° C., 5% CO2).

(2) Pre-protection of the cells: In the negative control group, 5, μL of PBS and 95 μL of Tyrode's buffer solution were added to each sample. In the blank control group, 5 μL of DNP-BSA and 95 μL of Tyrode's buffer solution were added to each sample. In the positive control group, 5 μL of loratadine (of various concentrations) and 95 μL of Tyrode's buffer solution were added to each sample. In the compound group, 5 μL of the compound solution (in PBS, with a final concentration of 1.25, 0. 625, 0.3125, 0.15625, 0.078125, or 0.0390625 μg/mL) and 95 μL of Tyrode's buffer solution were added to each sample. After the addition of above reagents, 95 μL of the cells were then added to culture plates, and incubated for 1 hour.

(3) Stimulating the cells: In the negative control group, 5 μL of PBS was added to each sample. In the other three groups, 5 μL of DNP-BSA was added to a final concentration of 1 μg/mL to stimulate the RBL-2H3 cells, and incubated for 1 hour.

(4) Disintegration of the cells: The culture supernatants were collected, and then the Tyrode's buffer solution (containing 0.1% of Triton X-100) was added to the culture plates to disintegrate the cells so as to obtain lysate solutions.

(5) β-hexosaminidase activity measurement: The supernatants and the lysate solutions were added to 96-well plates for fluorescent assays, 25 μL in each well, followed by the addition of 100 μL of 1.2 mM 4-methylumbelliferyl-N-acetyl-β-d-glucosaminide to allow reaction at 37° C. for 30 minutes. Then the fluorescence (excitation wavelength: 360 nm, emission wavelength: 450 nm) of the solution in each well was measured using a microplate reader.

(6) Calculation of degranulation efficiency:
Degranulation efficiency was calculated through the following expression:

$$\text{Degranulation efficiency}(\%) = \frac{FS}{FS + FL} \times 100\%$$

wherein, FS represent the fluorescence of supernatant, and FL represents the fluorescence of lysate solution.

(7) Calculation of inhibitory rate on allergy
Inhibitory rate was calculated with the following expression:

$$\text{Inhibitory rate (\%)} = \frac{DEB - DEC}{DEB - DEN} \times 100\%$$

wherein DEB represents the degranulation efficiency of blank control group, DEC represents the degranulation efficiency of compound group and DEN represents the degranulation efficiency of negative control group.

Results (Table 1) showed that the anthraquinone compound exhibited a strong inhibitory effect on mast cell degranulation, and thus could be used to prepare drugs for inhibiting mast cell degranulation. The further calculation indicated that the compound exhibited a strong anti-allergic activity, with an $IC_{50}$ of 1.87 μM ($IC_{50}$ refers to a concentration of the compound when the inhibitory rate is 50%), lower than that of loratadine (91.6 μM) of the positive control group, suggesting that the compound of the present invention could be used in anti-allergic drugs.

TABLE 1

Anti-allergic activity results

| Group | Concentration (μg/mL) | Degranulation efficiency (%) | Inhibitory rate (%) | $IC_{50}$ (μM) |
|---|---|---|---|---|
| Negative control group (PBS) | — | 10.86 | — | — |
| Blank control group (DNP-BSA) | — | 47.30 | — | — |
| Positive control group (loratadine) | — | — | — | 91.6 |
| Compound group | 1.25 | 14.29 | 90.59 | 1.87 |
|  | 0.625 | 24.46 | 62.67 |  |
|  | 0.3125 | 35.61 | 32.08 |  |
|  | 0.15625 | 38.46 | 24.25 |  |
|  | 0.078125 | 48.53 | −3.38 |  |
|  | 0.0390625 | 52.86 | −15.25 |  |

Accordingly, the compound disclosed herein may be combined with pharmaceutically acceptable carriers to form therapeutic compositions.

In one embodiment, an anti-allergic drug is provided comprising an effective dose of one or more of an anthraquinone compound and salts thereof as an active ingredient, and a pharmaceutically acceptable carrier. In another embodiment, a drug for inhibiting mast cell degranulation is provided comprising an effective dose of one or more of an anthraquinone compound and salts thereof as an active ingredient, and a pharmaceutically acceptable carrier.

Based on the disclosure and teachings of the foregoing description, those skilled in the art may also make appropriate changes and modifications to the above embodiments. Therefore, the present invention is not limited to the specific embodiments described above, and some modifications and changes to the present invention should also fall within the protection scope of the claims of the present invention. In addition, although some specific terms are used in this specification, these terms are just for convenience of explanation and do not constitute any limitation to the present invention.

What is claimed is:

1. A method for inhibiting mast cell degranulation, comprising administering to a subject in need thereof a composition comprising an effective amount of an anthraquinone compound or a salt thereof as an active ingredient, and a pharmaceutically acceptable carrier, wherein the anthraquinone compound has a structure according to formula (I):

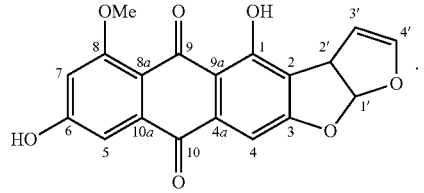

formula (I)

* * * * *